United States Patent [19]

Swedberg

[11] Patent Number: 5,089,103
[45] Date of Patent: Feb. 18, 1992

[54] ELECTROPHORESIS CAPILLARY WITH AGAROSE

[75] Inventor: Sally A. Swedberg, Los Altos, Calif.

[73] Assignee: Hewlett-Packard Company, Palo Alto, Calif.

[21] Appl. No.: 444,229

[22] Filed: Dec. 1, 1989

[51] Int. Cl.⁵ ............................................. G01N 27/26
[52] U.S. Cl. ............................... 204/182.8; 204/299 R
[58] Field of Search ........................... 204/299 R, 182.8

[56] References Cited

U.S. PATENT DOCUMENTS

| | | | |
|---|---|---|---|
| 3,876,376 | 4/1975 | Bauman et al. | 422/102 |
| 4,600,641 | 7/1986 | Ogawa et al. | 204/299 R |
| 4,675,300 | 6/1987 | Zare et al. | 204/180.1 |
| 4,680,201 | 7/1987 | Hjerten | 204/182.9 |
| 4,708,782 | 11/1987 | Andresen et al. | 204/180.1 |
| 4,810,456 | 3/1989 | Bente, III et al. | 204/180.1 |
| 4,865,706 | 9/1989 | Karger et al. | 204/182.8 |
| 4,865,707 | 9/1989 | Karger et al. | 204/299 R |
| 4,997,537 | 3/1991 | Karger et al. | 204/182.8 |

FOREIGN PATENT DOCUMENTS

| | | |
|---|---|---|
| 0162657 | 5/1987 | European Pat. Off. |
| 0341577 | 4/1989 | European Pat. Off. |
| 0324539 | 5/1989 | European Pat. Off. |
| WO87/05230 | 9/1987 | PCT Int'l Appl. |

OTHER PUBLICATIONS

Van Oss et al., "Simplified Cell Microelectrophoresis with Uniform Electroosmotic Backflow", Electrokinetic Sep Methods, 1979, pp. 111-20.

Van Oss et al., Chemical Abstracts, vol. 91, 153725u, 1979.

Maniatis et al., *Molecular Cloning*, 1982, p. 157.

Hjerten, Stellan, "High-Performance Electrophoresis Elimination of Electroendosmosis and Solute Adsorption", J. of Chromatography, 347, (1985), 191-198.

*Primary Examiner*—John Niebling
*Assistant Examiner*—David G. Ryser

[57] ABSTRACT

Capillary tubes useful for performing capillary zone electrophoresis separation techniques are prepared by precoating the capillary tubes with an adhesive agent, preferably a dilute agarose phase. The analytical agarose-based media then is positioned in the tubes, where it adheres to the earlier coating. The analytical media exhibits strong structural integrity and adheres well to the capillary tubes; moreover, the media is suitable for capillary zone electrophoretic separation of biopolymers.

12 Claims, No Drawings

ELECTROPHORESIS CAPILLARY WITH AGAROSE

FIELD OF THE INVENTION

The present invention generally relates to capillary zone electrophoresis of biopolymers and more particularly to a small bore capillary tube useful for electrophoretic separations of biopolymer solutes by means of an agarose-based media filling the capillary tube bore.

BACKGROUND OF THE INVENTION

Electrophoresis is a well-known technique for the separation of charged species by utilizing their differences in rate of migration under the influence of an electrical field. The prototype of all modern electrophoretic methods is free, or moving-boundary, electrophoresis. The mobility $\mu$ in square centimeters per volt-second of a molecule in an electric field is given by the ratio of the velocity of migration v, in centimeters per second, to electric field strength E, in volts per centimeter: $\mu = V/E$. For small ions, such as chloride, $\mu$ is between 4 and $9 \times 10^{-4} cm^2 v^{-1} s^{-1}$ (25° C.); for proteins, it is about 0.1 to $1.0 \times 10^{-4} cm^2 v^{-1} s^{-1}$. Protein thus migrates much more slowly in an electrical field than small ions simply because they have a much smaller ratio of charge to mass.

Free electrophoresis has been largely supplanted by various forms of zone electrophoresis in which the aqueous protein solution is immobilized in a solid matrix that provides mechanical rigidity and reduces convection and vibration disturbances. Matrix material that is porous also allows for sieving. This form of zone electrophoresis can separate a protein mixture on the basis of both electric charge and molecular size, thereby providing high resolution.

Capillary zone electrophoresis ("CZE") in small bore capillaries was first demonstrated by Jorgenson and Lukacs, and has proven useful as an efficient method for the separation of certain small solutes. *J. Chromatog.*, 218 (1981), page 209; *Anal. Chem.*, 53 (1981) page 1298. Attractive factors for CZE include the small sample sizes, little or no sample pretreatment, high resolution, automation, and the potential for quantification and recovery of biologically active samples. For example, U.S. Pat. No. 4,675,300, inventors Zare et al., issued June 23, 1987 describes theories and equipment for electrokinetic separation processes employing a laser-excited fluorescence detector. The system described by Zare et al. includes a fused silica capillary with a $75\mu$ inner diameter.

CZE can be strongly influenced by electroosmosis, which is the flow of liquid that occurs when an electrical potential is applied to a liquidfilled porous medium. Jorgenson and Lukacs reported that separation of model proteins, such as cytochrome, lysozyme and ribonuclease A, in untreated fused silica capillaries with a phosphate buffer at pH 7 was complicated by the adsorption of proteins to the surface of the capillaries. They concluded that adsorption affects electropherograms in two undesirable ways. First, it leads to broad asymmetric "tailed" zones. Second, adsorbed proteins modified the capillary surface, usually decreasing electroosmotic flow significantly which leads to unpredictable migration for all sample zones upon repeated injection. Jorgenson and Lukacs, *Science*, 222 (1983) page 266.

Electrophoresis in large diameter capillaries may be attended by a hydrodynamic reflow, which causes the zones to become strongly parabolically distorted. A reflow occurs when the resistance to hydrodynamic flow in the electrophoresis tube is relatively low. Reflow becomes more problematic as the inner diameter of the tube increases. Another phenomenon associated with large diameter open tubes is the problem of convection.

It has been reported that coating electrophoresis tubes with a mono-molecular layer of a non-crosslinked polyacrylamide significantly reduces the electroendosmosis effect. Hjerten, S., *J. Chromatography*, 347 (1985), 191-198. Moreover, the use of anticonvective agents in capillaries reduced the convection problem and allows for the use of higher inner diameter capillaries.

Lauer and McManigill, *Anal. Chem.*, 58 (1986), page 166, have reported that the Coulombic repulsion between proteins and the capillary wall of silica capillaries can overcome adsorption tendencies of the proteins with the capillary wall. They demonstrated separations of model proteins (ranging in molecular weight from 13,000 to 77,000) by varying the solution pH relative to the isoelectric point (pI) of the proteins to change their net charge.

Increasing the selectivity control of capillary electrophoresis has been achieved through the use of anionic micelles from sodium dodecyl sulfate (SDS). This approach has been used to separate bases, nucleosides and nucleotides in a buffer solution with a pH of 7. Since the bases and nucleosides are uncharged at the pH of operation, separation is a result of differential partition within the interior of the micelle; the more hydrophobic the species, the larger the partition coefficient and the larger the retention. Oligonucleotides are negatively charged and can be separated without SDS micelles; however, the time window is narrow and separation of complex mixtures is limited. The combination of low concentrations of divalent metals and SDS micelles leads to a significant enhancement of the time window and good separation of oligonucleotides. The metal ion is electrostatically attracted to the surface of the micelle and differential metal complexation of the oligonucleotides with the surface of micelles leads to separation of complex mixtures. See Cohen, *Anal. Chem.*, 59 (1987) 1021-27.

Gels as a CZE media are difficult to retain in the capillary tubing. One possible explanation is that an electric double layer forms with the gel structure at the gel-solution interface which causes an appreciable electrostatic flow (EOF) component. Moreover, charged groups within the gel structure may be present. Therefore, between the considerable EOF component and the tendency of the gel to electrophorese due to its own charge, there is a net movement of the gel unless the gel is sufficiently adhered to the surface of the capillary tube.

U.S. Pat. No. 4,810,456, inventors Myerson et al., issued March 7, 1989, describes a method for preparing electrophoretic gel that is substantially free of defects caused by shrinkage that generally accompanies polymerization. The procedure consists of compressing the prepolymer-bearing (e.g., monomer) to a density within a predetermined range and maintaining the density of the substance during polymerization.

U.S. Pat. No. 4,680,201, inventor Hjerten, issued July 14, 1987, describes a method for preparing a thin-wall, narrow-bore capillary tube for free electrophoretic separations by use of a bifunctional compound in which one group reacts specifically with the glass wall and the other with a monomer taking part in a polymerization process. This procedure results in a polymer coating, such as polyacrylamide coating, and is suggested for use in coating other polymers, such as poly(vinyl alcohol) and poly(vinylpyrrolidone). The method purportedly overcomes problems associated with adsorption and electroendosmosis, but this approach introduces a coating phase consisting of material different from the gel medium. Moreover, this method is limited to gel media formed by polymerization such as polyacrylamide which may contain potentially damaging polymerization by-products.

SUMMARY OF THE INVENTION

It is an object of the present invention to provide capillary tubes with agarose gel based media that are useful for electrophoretic separations of solutes and in which the medium substantially adheres to the surface of the tubes.

It is another object of the present invention to provide capillary tubes useful for rapid electrophoretic separations of biopolymers, such as protein and oligonucleotide solutes, based, at least in part, on charge differences and with substantially quantitative results. Other objects and advantages of the invention will be apparent to those skilled in the art to which the invention pertains.

In one aspect of the present invention, a small bore capillary tube useful for electrophoretic separations of biopolymer solutes comprises an agarosebased media that is adherently disposed in and fills the bore along at least a portion of the tube length. The media is permeable to biopolymers, such as protein and oligonucleotide solutes, moving in response to sufficient electric current for biopolymer separations. The agarose-based media fills the bore along the tube portion as a continuous phase, and is adapted to maintain continuity when subjected to an applied electric field of about 300 volts per centimeter of tube length. Usual capillary bore diameters are between about 75$\mu$ to about 500$\mu$. The agarose media preferably includes a polyol to increase mechanical stability and serves as an anticonvective polymer effective to increase a path length of optically detectable species passing through the media during separations.

Capillary tubes of the invention are preferably prepared by first coating the bore with an adhesive agent, such as a dilute agarose phase. The analytical agarose-based media, including for example, agarose in amount from about 0.5 wt. % to about 5 wt. %, then is positioned in and fills the tube and adheres to the earlier coating of dilute agarose phase with surprisingly strong adhesive forces despite the small mass of gelled media within the tube on one hand and the strength of the electric field typically applied for separations on the other hand.

DETAILED DESCRIPTION OF THE PREFERRED EMBODIMENTS

Small bore capillary tubes useful in capillary zone electrophoresis usually have bore diameters less than about 500$\mu$, often less than about 200$\mu$. Typical bore sizes for use with the present invention are from about 75$\mu$ to about 500$\mu$, more usually about 75$\mu$ to about 200$\mu$. These small bore capillary tubes are filled along at least a portion of the tube length, preferably entirely filled, with an agarose-based media that is adherent to the bore surface and is permeable to the solutes being separated in response to sufficient of an applied electric field in accordance with the invention.

Capillary tubes of the invention are useful in separating biopolymer solutes by means of capillary zone electrophoresis. By "biopolymer" is meant, for example, naturally occurring macromolecules, such as proteins and oligonucleotides. The predominate mechanism of separation for the inventive tubes is by differences in charge, although the relatively loose agarose network can provide some small amount of molecular weight sieving. However, agarose gels can be prepared in which significant molecular weight sieving occurs.

Because of the small bore diameter, simply filling the tubes with the analytical quality agarosebased media has been found to lead to extrusion, or displacement and discontinuity of structure during application of the typical electric fields used in electrophoretic separations. Extrusion or displacement and formation of discontinuities, of course, destroy the quantitative nature of the separation, and leads to mixing of zones of the separating species. Attempts to retard the extrusion, such as by use of a cap or screen on the tube, also leads to discontinuities in the gelled media and distorts the mobilities of the separating species.

The present invention, however, provides that an agarose-based media is not only adherently disposed in the capillary bore, but is also adapted to maintain continuity of the continuous agarose-based phase when subjected to a field of, for example, about 300 V/cm in intensity.

Agarose is a natural polysaccharide isolated form agar and agarose gel is a relatively transparent anticonvection medium that prevents broadening of the zones during separation. Agarose is essentially biologically inert and non-toxic, unlike polyacrylamide. Moreover, agarose contains no potentially damaging polymerization byproducts since there is no freeradical polymerization involved in agarose gelation.

Agarose generally is considered the medium of choice for separation by molecular weight of large macromolecules ($\geq$500,000 daltons) and is the preferred gel matrix for resolving nucleic acids. Unlike crosslinked polyacrylamide gels, agarose forms firm, mechanically stable gels at low concentrations yielding a macroporous matrix. These properties of gel strength and macroporosity are possible because, during gelation, agarose molecules associate into double helices which then further aggregate to form a rigid matrix of suprafibers. See Serwer, P., "Agarose Gels: Properties and Use for Electrophoresis", Electrophoresis, 4 (1983), 375-382. Sieving in agarose is dependent on gel concentration and can therefore be increased by increasing the percentage of agarose in the gel. Derivatization of agarose, e.g., by hydroxyethylation, has been observed to increase the sieving properties of these gels. It has been proposed that hydroxyethylation causes a decrease in the number of agarose double helices per suprafiber resulting in reduced pore sizes. Serwer, P., et al., "Agarose Gel Electrophoresis of Bacteriophages and Related Particles. III. Dependence of Gel Sieving on the Agarose Preparation", *Electrophoresis*, 4 (1983), 233-236, incorporated herein by reference.

Various additives may be included in agarose modify the properties of the matrix. For example, polyols can be used to increase mechanical stability, probably by increased hydrogen bonding, in the gelled media and to assist in adhesiveness. Illustrative polyols useful for this purpose include sorbitol, sucrose, erythritol and polyethylene glycol. Appropriate amounts of such additional components are in a range from about 0.5% to 10%.

Aspects of the present invention will now be demonstrated by the following examples.

EXAMPLE I

Preparation of capillary tubes

A 0.1% agarose mixture (SeaKem ® LE Lot No. 71594) was prepared and allowed to cool slightly until its consistency was clot-like. 3 × 50 cm lengths of 200 i.d. × 330 o.d. capillary tubing (Polymicro Technologies) were used. The mixture was pumped through the tubes for approximately ten minutes. Thereafter, the tubes were flushed with helium and the coating was allowed to sit overnight.

The analytical gel consisted of 1% agarose with 10% (W/V) sorbitol. The analytical gel mixture was pumped through the precoated tubes while the mixture was kept molten. The analytical gel was then allowed to sit overnight.

EXAMPLE II

Examination for extrusion

A capillary prepared by the inventive method as described in Example I was placed in a normal position on a detector mount of a modified IFCO UV visible detector. It was connected to the electrodes, without being placed in the detector, to test whether extrusion would occur under the influence of electric fields of increasing intensity. After 31 minutes at 100 V/cm (30 $\mu$A), no extrusion was visually or electrically evident. Next, the capillary was subject to a field intensity of 200 V/cm (90 $\mu$A) for 45 minutes, and again, no extrusion was detected Thereafter, the capillary tube was inspected under a binocular dissecting microscope and no discontinuities in the gel were found.

EXAMPLE III

Isoelectric focusing

Capillaries prepared by the inventive method were used to separate three structurally related lentil lectins (Pharamacia Fine Chemicals), proteins that are commonly used in isoelectric focusing kits as standards with isoelectric points of 8.15, 8.35, and 8.55, respectively. Applying the test samples to capillaries of the invention and using CZE resolved the three proteins whereas the same mixture of proteins on a prior art capillary tube without agarose] and using CZE did not resolve the three proteins. A 250 mM phosphate buffer at pH 7 was used.

It is to be understood that while the invention has been described above in conjunction with preferred specific embodiments, the description and examples are intended to illustrate and not limit the scope of the invention, which is defined by the scope of the appended claims.

It is claimed:

1. A method for preparing a narrow-bore capillary tube for use in electrophoretic separations comprising the steps of:

contacting a dilute agarose phase wit the bore of the tube to for m a precoat thereon; and adherently filling the bore with an agarose-based analytical gel along at least a portion of the tube which is precoated with the dilute agarose phase.

2. The method as defined in claim 1 wherein the analytical gel is adapted for separation of biopolymers substantially based on charge differences.

3. The method as defined in claim 2 wherein the analytical gel has an agarose concentration from about 0.5 wt. % to about 5 wt. %.

4. The method as defined in claim 3 wherein the gel is adapted to separate biopolymer solutes by molecular sieving.

5. An apparatus useful for electrophoretic separations of bipolymer solutes comprising:

a capillary tube defining a bore surface;

a precoat adherently coating at least a portion of the bore surface, the precoat including an agarose phase; and an analytical agarose-based gel adhered in the capillary, which gel is adherent to the precoat and is permeable to biopolymer solutes moving in response to sufficient electric current for separation of the biopolymers.

6. The apparatus as defined in claim 5 wherein the analytical gel fills the capillary as a continuous phase, and the analytical gel is adapted to maintain continuity when subjected to an applied field of between about 300 V/cm to about 400 V/cm tube length.

7. The apparatus as defined in claim 12 wherein the analytical gel has an agarose concentration from about 0.5 wt. % to about 5 wt. %.

8. The apparatus as defined in claim 7 wherein the gel is adapted to separate biopolymer solutes by molecular sieving.

9. The apparatus as defined in claim 5 wherein the analytical gel is adapted for separation of bipolymers substantially based on charge differences.

10. An apparatus useful for electrophoretic separations of biopolymer solutes comprising:

a capillary tube having a bore size between about 75 $\mu$ to about 500 $\mu$ and defining a bore surface; and, an agarose-based media being permeable to biopolymer solutes and disposed within the bore as a continuous gelled phase, the agarose-based media radially outwardly extending to the bore surface and adhered thereto and longitudinally extending along sufficient of the tube length to separate biopolymers substantially on the basis of charge differences, the agarose-based media being sufficiently stable as to maintain continuity when subjected to an electric field of about 300 V/cm tube length.

11. The apparatus of claim 10 wherein the agarose-based media includes agarose in an amount from about 0.5 wt. % to about 5 wt. %, and further includes an additive effective to increase mechanical stability in an amount from about 0.5% to about 10%, the agarose-based media being adhered to the bore surface by an adhesive agent.

12. The apparatus of claim 11 wherein the adhesive agent is effective to maintain the media adhered to the bore surface during separations of biopolymers by adhesive forces, and the adhesive agent includes agarose.

* * * * *